(12) United States Patent
Kobold et al.

(10) Patent No.: US 11,585,811 B2
(45) Date of Patent: Feb. 21, 2023

(54) IMMOBILIZED ANALYTES

(71) Applicant: Roche Diagnostics Operations, Inc., Indianapolis, IN (US)

(72) Inventors: Uwe Kobold, Weilheim (DE); Robert Lang, Munich (DE); Andreas Leinenbach, Oberhausen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 246 days.

(21) Appl. No.: 16/389,066

(22) Filed: Apr. 19, 2019

(65) Prior Publication Data

US 2019/0250158 A1    Aug. 15, 2019

Related U.S. Application Data

(63) Continuation of application No. PCT/EP2017/076961, filed on Oct. 23, 2017.

(30) Foreign Application Priority Data

Oct. 24, 2016 (EP) .................................... 16195304

(51) Int. Cl.
  *G01N 33/53* (2006.01)
  *G01N 33/566* (2006.01)
  *G01N 33/68* (2006.01)
  *G01N 33/543* (2006.01)
  *G01N 33/573* (2006.01)

(52) U.S. Cl.
  CPC ......... *G01N 33/566* (2013.01); *G01N 33/543* (2013.01); *G01N 33/573* (2013.01); *G01N 33/6848* (2013.01)

(58) Field of Classification Search
  None
  See application file for complete search history.

(56) References Cited

U.S. PATENT DOCUMENTS

| | | | |
|---|---|---|---|
| 6,627,457 B2* | 9/2003 | Pandian ................. | G01N 33/76 435/7.1 |
| 8,030,085 B2* | 10/2011 | Amano ............ | G01N 33/57434 436/87 |
| 8,198,063 B1* | 6/2012 | Baginski .................. | C12N 9/80 435/200 |
| 8,486,641 B2* | 7/2013 | Karin ...................... | C07K 16/24 435/7.1 |
| 2004/0253659 A1* | 12/2004 | Rasamoelisolo .. | G01N 33/6818 435/23 |
| 2005/0164411 A1 | 7/2005 | Kim | |

FOREIGN PATENT DOCUMENTS

| | | |
|---|---|---|
| CA | 2527650 A1 | 12/2004 |
| CN | 1700009 A | 11/2005 |
| CN | 101358969 A | 2/2009 |
| CN | 103038631 A | 4/2013 |
| CN | 105324489 A | 2/2016 |
| CN | 105579849 A | 5/2016 |
| CN | 2017800658713 A | 6/2019 |
| EP | 0404097 A2 | 12/1990 |
| JP | 2004537728 A | 12/2004 |
| JP | 2011522210 A | 7/2011 |
| WO | 1993/001161 A1 | 1/1993 |
| WO | 2006128362 A1 | 12/2006 |
| WO | 2008145763 A1 | 4/2008 |
| WO | 2011112188 A1 | 9/2011 |
| WO | 2012129611 A1 | 10/2012 |
| WO | 2014138132 A2 | 9/2014 |
| WO | 2014195899 A1 | 12/2014 |
| WO | 2016011082 A1 | 1/2016 |
| WO | 2016097116 A1 | 6/2016 |
| WO | 2018077783 A1 | 5/2018 |

OTHER PUBLICATIONS

Strongin, Laboratory Diagnosis of Viral INfections, Sensitivity, Specificity, and Predictive Value of Diagnostic Tests: Definitions and Clinical Applications, Lennette, ed. Marcel Dekker, Inc. New York, pp. 211-219, 1992. (Year: 1992).*
Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
Ahmad-Tajudin, Asilah et al., MALDI-target integrated platform for affinity-captured protein digestion, Analytica Chimica Acta, 2014, pp. 1-8, vol. 807.
Ahn, Yeong Hee et al., Quantitative Mass Spectrometric Analysis of Glycoproteins Combined with Enrichment Methods, Mass Spectrometry Reviews, 2014, pp. 148-165, vol. 34.
Bailey, Ulla-Maja and Schulz, Benjamin L., Deglycosylation systematically improves N-glycoprotein identification in liquid chromatography-tandem mass spectrometry proteomics for analysis of cell wall stress responses in *Saccharomyces cerevisiae* lacking Alg3p, Journal of Chromatography B, 2013, pp. 16-21, vol. 923-924.
Galfrè, G. and Milstein C., Preparation of Monoclonal Antibodies: Strategies and Procedures, Methods in Enzymology, 1981, pp. 3-46, vol. 73.

(Continued)

*Primary Examiner* — Gary Counts
(74) *Attorney, Agent, or Firm* — Stinson LLP

(57) ABSTRACT

A method for detecting an analyte involving a) contacting the analyte, a capture agent and a solid surface to form a capture complex attached to a solid surface, b) cleaving at least one covalent bond within the analyte and/or within said capture agent in the capture complex and, thereby, releasing the analyte or a fragment thereof from the capture complex, and c) detecting at least one fragment of the analyte and, thereby, detecting the analyte is disclosed herein. A kit having i) a capture agent binding to an analyte; and ii) an agent cleaving at least one covalent bond within the analyte and/or within the capture agent; and to the use of a protease for releasing fragments of an analyte for detecting the analyte, wherein the analyte is bound to a solid surface via a capture agent is also disclosed herein.

15 Claims, 6 Drawing Sheets

Specification includes a Sequence Listing.

(56) References Cited

OTHER PUBLICATIONS

Holliger, Philipp et al., "Diabodies": Small bivalent and bispecific antibody fragments, Proceedings of the National Academy of Sciences USA, 1993, pp. 6444-6448, vol. 90.

Hudson, Peter J. and Souriau, Christelle, Engineered antibodies, Nature Medicine, 2003, pp. 129-134, vol. 9, No. 1.

International Search Report dated Jan. 3, 2018, in Application No. PCT/EP2017/076961, 2 pp.

Klee, Eric W. et al., Mass Spectrometry Measurements of Prostate-Specific Antigen (PSA) Peptides Derived From Immune-Extracted PSA Provide a Potential Strategy for Harmonizing Immunoassay Differences, American Journal of Clinical Pathology, 2014, pp. 527-533, vol. 141.

Krastins, Bryan et al., Rapid development of sensitive, high-throughput, quanlitative and highly selective mass spectrometric targeted immunoassays for clinically important proteins in human plasma and serum, Clinical Biochemistry, 2013, pp. 399-410, vol. 46.

Köhler, G. and Milstein, C., Continuous cultures of fused cells secreting antibody of predefined specificity, Nature, 1975, pp. 495-497, vol. 256.

Liu, Tao et al., Human Plasma N-Glycoproteome Analysis by Immunoaffinity Subtraction, Hydrazide Chemistry, and Mass Spectrometry, Journal of Proteome Research, 2005, pp. 2070-2080, vol. 4, No. 6.

Lopez, Mary F. et al., Selected Reaction Monitoring-Mass Spectrometric Immunoassay Responsive to Paiathyroid Hormone and Related Variants, Clinical Chemistry, 2010, pp. 281-290, vol. 56, Issue 2.

Peracaula, Rosa et al., Altered glycosylation pattern allows the distinction between prostate-specific antigen (PSA) from normal and tumor origins, Glycobiology, 2003, pp. 457-470, vol. 13, No. 6.

Peterman, Scott et al., An automated, high-throughput method for targeted quantification of intact insulin and its therapeutic analogs in human serum or plasma coupling mass spectrometric immunoassay with high resolution and accurate mass detection (MSIA-HR/AM), Proteomics, 2014, pp. 1445-1456, vol. 14.

Popp, Robert et al., An automated assay for the clinical measurement of plasma renin activity by immuno-MALDI (iMALDI), Biochimica et Biophysica Acta, 2015, pp. 547-558, vol. 1854.

Prakash, Amol et al., Interlaboratory Reproducibility of Selective Reaction Monitoring Assays Using Multiple Upfront Analyte Enrichment Strategies, Journal of Proteome Research, 2012, pp. 3986-3995, vol. 11.

Trenchevska, Olgica et al., Development of multiplex mass spectrometric immunoassay for detection and quantification of apolipoproteins C-I, C-II, C-III and their proteoforms, Methods, 2015, pp. 86-92, vol. 81.

Yassine, Hussein et al., Mass spectrometric immunoassay and MRM as targeted MS-based quantitative approaches in biomarker development: Potential applications to cardiovascular disease and diabetes, Proteomics Clinical Applications, 2013, pp. 528-540, vol. 7.

Zhao, Lei et al., Quantification of Proteins Using Peptide Immunoaffinity Enrichment Coupled with Mass Spectrometry, Journal of Visualized Experiments, 2011, 5 pp., vol. 53, e2812.

Klee et al., Mass Spectometry Measurements of Prostate-Specific Antigen (PSA) Peptides Derived From Immune-Extracted PSA Provide a Potential Strategy for Harmonizing Immunoassay Differences; AJCP, 2014, vol. 141, pp. 527-533.

\* cited by examiner

IMMOBILIZED ANALYTES

CROSS-REFERENCE TO RELATED APPLICATIONS

This application is a continuation of International Application No. PCT/EP2017/076961 filed Oct. 23, 2017, which claims priority to European Application No. 16195304.7 filed Oct. 24, 2016, the disclosures of which are hereby incorporated by reference in their entirety.

BRIEF SUMMARY OF THE INVENTION

The present invention relates to a method for detecting an analyte comprising a) contacting said analyte, a capture agent and a solid surface to form a capture complex attached to a solid surface, b) cleaving at least one covalent bond within said analyte and/or within said capture agent comprised in said capture complex and, thereby, releasing said analyte or a fragment thereof from said capture complex, and c) detecting said at least one fragment of said analyte and, thereby, detecting said analyte. The present invention further relates to a kit comprising i) a capture agent binding, in an embodiment specifically binding, to an analyte; and ii) an agent cleaving at least one covalent bond within said analyte and/or within said capture agent; and to a use of a protease for releasing fragments of an analyte for detecting said analyte, wherein said analyte is attached to a solid surface via a capture agent.

BACKGROUND OF THE INVENTION

Agents specifically binding to analytes, in particular antibodies, have been used for a long time in the enrichment of analytes. The typically high affinity of an antibody to its cognate epitope usually is an advantage, since it allows for detection even of small amounts of analyte. The high affinity, however, turns into a disadvantage when it is attempted to recover the analyte from the analyte/antibody complex, since very harsh conditions have to be applied. Moreover, the conditions and buffers which must be applied usually are not compatible with downstream applications, making further steps of buffer change, precipitation, and the like necessary, which often reduce recovery of the analyte significantly. Exemplary applications relating to such methods, in particular in the field of mass spectrometry (MS), are provided in, e.g. Krastins et al. (2013), Clinical biochemistry 46: 399-410; Lopez et al. (2010), Clinical chemistry 56: 281-290; Peterman et al. (2014), Proteomics 14: 1445-1456; Prakash et al. (2012), Journal of proteome research 11: 3986-3995; Trenchevska et al. (2015), Methods (San Diego, Calif.) 81: 86-92; Yassine et al. (2013), Proteomics Clinical applications 7: 528-540; Popp et al. (2015), Biochimica et biophysica acta 1854: 547-558; Zhao et al. (2011), Journal of Visualized Experiments 53: e2812 1-5; and in Klee et al. (2014), Am J Clin Pathol 141:527).

Further, in the field of polypeptide analysis, it was found that glycosylation of proteins may severely hamper analysis, in particular analysis requiring enzymatic treatment of such glycosylated proteins, like proteolysis, which may be required e.g. in MS methods. To solve this problem, CA2527650 proposed a stepwise method for identification of glycosylated polypeptides. The steps of the method involve treatment of a biological sample containing a glycosylated polypeptide with at least one protease to begin peptide digestion, followed by deglycosylation and subsequent redigestion with at least one protease to result in deglycosylated polypeptide fragments. The deglycosylated polypeptide fragments are then sequenced using mass spectrometry and identified by sequence comparison with a database of known sequences.

Nonetheless, there is still a need for efficient methods for providing polypeptides obtained by immunological methods for downstream applications like, e.g. mass spectrometry. This problem is solved by the means and methods of the present invention, with the features of the independent claims. Preferred embodiments, which might be realized in an isolated fashion or in any arbitrary combination are listed in the dependent claims.

DETAILED DESCRIPTION OF THE INVENTION

Figure 1A:
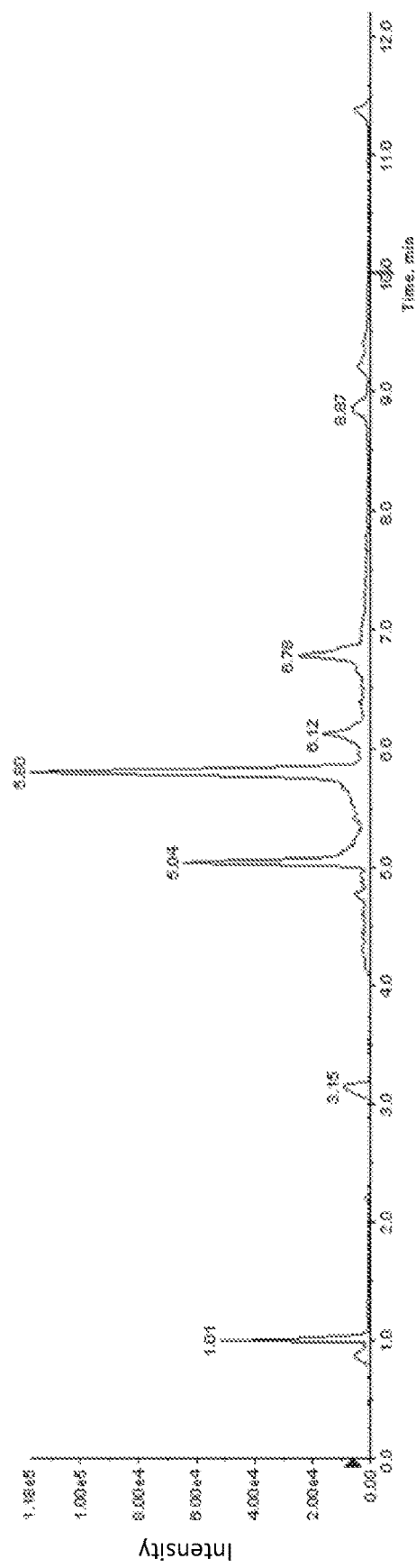
FIG. 1A: Reconstructed Total Ion Current Chromatogram (RTICC) showing detection of fragments of PSA produced by deglycosylation and protease treatment in solution as described in the Examples. A first fragment with an elution time of 8.15 min is not generated; a second fragment with an elution time of 5.80 min is generated by proteolysis alone, independently of deglycosylation; x-axis: elution time in min, y-axis: intensity in counts per second (cps).

The present invention relates to a method for detecting an analyte comprising
a) contacting said analyte, a capture agent and a solid surface to form a capture complex attached to a solid surface, b) cleaving at least one covalent bond within said analyte and/or within said capture agent comprised in said capture complex and, thereby, releasing said analyte or a fragment thereof from said capture complex, and c) detecting said analyte or fragment thereof and, thereby, detecting said analyte.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, as used in the following, the terms "preferably", "more preferably", "most preferably", "particularly", "more particularly", "specifically", "more specifically" or similar terms are used in conjunction with optional features, without restricting further possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding further embodiments of the invention, without any restrictions regarding the scope of the invention and without any restriction regarding the possibility of combining the features introduced in such way with other optional or non-optional features of the invention. Moreover, if not otherwise indicated, the term "about" relates to the indicated value with the commonly accepted technical precision in the relevant field, in an embodiment relates to the indicated value ±20%, in a further embodiment ±10%, in a further embodiment ±5%.

The method for detecting an analyte of the present invention, in an embodiment, is an in vitro method. Moreover, it may comprise steps in addition to those explicitly mentioned above. For example, further steps may relate, e.g., to obtaining a sample comprising an analyte for step a), or structurally modifying, e.g. derivatizing the at least one fragment of the analyte after step b). Moreover, one or more of said steps may be performed by automated equipment.

The term "analyte", as used herein, refers to a chemical compound capable of being bound, in an embodiment specifically bound, by a capture agent and comprising at least one cleavable bond. In an embodiment, said cleavable bond is a bond cleavable by an enzyme. In an embodiment, cleavage of said cleavable bond causes the analyte to be bound by a capture agent with an affinity at least 10 fold, in a further embodiment at least 100 fold lower than the affinity of said capture agent for said analyte. In a further embodiment said cleavage of said cleavable bond causes at least one fragment of said analyte to be released from said analyte; in particular causes the halftime of capture complex dissociation to decrease to a value of less than 2 min, in an embodiment of less than 1 min, in a further embodiment of less than 30 s, in a further embodiment of less than 10 s, in a further embodiment of less than 1 s. In a further embodiment, the analyte is a compound produced by or consumed in the metabolism of a subject. In an embodiment, the term relates to at least one molecule of a specific analyte up to a plurality of molecules of said specific analyte. An analyte in accordance with the present invention encompasses all classes of organic or inorganic chemical compounds, including those being comprised by biological material, such as organisms. In an embodiment, the analyte is a small molecule. In a further embodiment, the analyte is a macromolecule, in an embodiment a biological macromolecule, in a further embodiment a polynucleotide or a polypeptide. Thus, in an embodiment, the analyte is a chemical compound with a molecular mass of at least 2000 u (2000 Da; 1 u=1.66× $10^{-27}$ kg), in a further embodiment of at least 5000 u, in a further embodiment, of at least 10000 u. In an embodiment, the analyte is a chemical compound with a molecular mass of from 2 kDa to 500 kDa, in an embodiment of from 5 kDa to 250 kDa.

In an embodiment, the analyte is a polypeptide. As is known to the skilled person, a polypeptide, in particular a natural polypeptide, consists of amino acids connected via covalent peptide bonds. As is also known to the skilled person, side chains of amino acids may be further modified, e.g. by acetylation, phosphorylation, and/or glycosylation, in particular in eukaryotic cells. Thus, the analyte may also be a modified polypeptide, in particular a posttranslationally modified polypeptide, e.g. a glycosylated polypeptide. It is, however, also envisaged by the present invention that the analyte is a polypeptide modified with non-naturally occurring side chains, e.g. a PEGylated polypeptide. In an embodiment, the analyte is PSA. In an embodiment, the analyte is human PSA (Genbank Acc No NP_001639.1 GI:4502173) or one or all of its isoforms and/or one or all of its mature forms.

The term "covalent bond" is understood by the skilled person. In an embodiment, the covalent bond of the present invention is cleavable, in an embodiment is enzymatically cleavable. In an embodiment, the covalent bond of the present invention is hydrolyzable, in a further embodiment enzymatically hydrolyzable. In an embodiment, the covalent bond involves at least one carbon atom. In a further embodiment, the covalent bond is a C—O or a C—N bond. Thus, in an embodiment, the covalent bond of the present invention is an ester bond, a glycosidic bond, or an amide bond, in particular a peptide bond. In an embodiment, the covalent bond of the present invention is a peptide bond. As used herein, the "backbone covalent bonds" of a chemical molecule are the covalent bonds forming the longest possible chain of covalent bonds within the molecule. In a polypeptide, the backbone covalent bonds are the bonds forming the peptide bonds within the polypeptide. Correspondingly, the "non-backbone covalent bonds" are covalent bonds branching off the backbone covalent bond or are comprised in a branched-off chain of covalent bonds. Accordingly, in a polypeptide, covalent bonds within side chains of amino acids or within modifications thereof, e.g. in glycosylated side chains, are non-backbone covalent bonds.

In an embodiment, the analyte is a polypeptide and cleaving at least one covalent bond within said analyte comprises hydrolyzing, in an embodiment enzymatically hydrolyzing, at least one peptide bond within said analyte. In an embodiment, cleaving at least one covalent bond within said analyte comprises contacting said analyte with at least one protease. In an embodiment, the protease is a protease for which the substrate specificity is known. In a further embodiment, the protease is an endopeptidase, in a further embodiment, the protease is Chymotrypsin, Pepsin, Elastase, Thermolysin, Proteinase K, LysC, GluC, Trypsin or Endoproteinase ArgC (Clostripain), in a further embodiment is Trypsin or Endoproteinase ArgC (Clostripain), in a further preferred embodiment, the protease is Trypsin.

As will be understood by the skilled person, the analyte may be contacted with more than one of the aforesaid enzymes cleaving at least one covalent bond, in particular with at least two, at least three, or at least four enzymes cleaving at least one covalent bond. In an embodiment, contacting the analyte with more than one enzyme cleaving at least one covalent bond is performed sequentially; in a further embodiment, contacting the analyte with more than one enzyme cleaving at least one covalent bond is performed simultaneously, i.e. by contacting the analyte with at least two or more of said enzymes cleaving at least one covalent bond at the same time. The skilled person knows how to select hydrolysis conditions in such case. The skilled person, however, is aware that not all combinations of said enzymes may be compatible e.g. for different requirements regarding reaction temperature, pH, cofactors, or ions and, in case of incompatibility, will consider sequential treatment. Accordingly, e.g. contacting an analyte with at least one protease and at least one glycosidase as specified herein, in an embodiment, is accomplished by sequential contacting; in a further embodiment, contacting an analyte with at least one protease and at least one glycosidase as specified herein is accomplished by simultaneous contacting. Also, e.g. contacting an analyte with at more than one protease as specified herein, in an embodiment, is accomplished by sequential contacting with the respective protease; in a further embodiment, contacting an analyte with at more than one protease as specified herein is accomplished by simultaneous contacting with at least two proteases.

According to the present invention, cleavage of at least one covalent bond within said analyte and/or within said capture agent releases the analyte or at least one fragment thereof from the capture complex. As used herein, the term "release" relates to bringing the analyte, a fragment thereof, or the capture agent into a state causing dissociation of said analyte or fragment thereof from the capture complex. Thus, in case the capture agent is attached to a solid surface, release of the analyte or of a fragment thereof enables elution of said analyte or of a fragment thereof from the solid surface. Thus, in an embodiment, the dissociation constant between the analyte or a fragment thereof and the residual capture complex after cleavage of at least one covalent bond is at least $10^{-4}$ mol/l, in an embodiment at least $10^{-3}$ mol/l, in a further embodiment at least $10^{-2}$ mol/l, in a further embodiment at least 0.1 mol/l. In an embodiment, at least two covalent bonds within said analyte and/or within said capture agent are cleaved, e.g. releasing an internal peptide from a polypeptide. In a further embodiment, a multitude of covalent bonds is cleaved, wherein said multitude is, in an embodiment at least five, in a further embodiment at least ten, in a further embodiment at least 25 covalent bonds.

In an embodiment, at least one fragment released from said analyte is a specific fragment of said analyte, the term "specific fragment" relating to a fragment allowing identification of said analyte by means of said specific fragment. The skilled person understands that identification of an analyte by means of one of its fragments depends on the detection method selected. E.g. a specific fragment may be a fragment having a specific elution time in an LC and/or may be a fragment providing a specific m/z ration in an MS, or the like.

In an embodiment, the analyte is comprised in a sample, in an embodiment in a sample of a subject. The term "sample", as used herein, refers to any sample suspected or known to comprise an analyte. It is envisaged according to the present invention that the sample may be, e.g. a food sample, a sample of cell culture supernatant, or a sample of tissue or bodily fluid of a subject. In an embodiment, the sample is a sample of a body fluid, a sample of separated cells, a sample from a tissue or an organ, or a sample of wash/rinse fluid obtained from an outer or inner body surface of a subject. In an embodiment, the sample is body fluid like blood, plasma, serum, urine, saliva, lacrimal fluid. In an embodiment, the sample is a stool sample. Samples can be obtained by well-known techniques and include, in an embodiment, scrapes, swabs or biopsies. Samples can be obtained by use of brushes, (cotton) swabs, spatula, rinse/wash fluids, punch biopsy devices, puncture of cavities with needles or surgical instrumentation. Separated cells and/or cell-free liquids may be obtained from cell culture supernatants, body fluids, or the tissues or organs by separating techniques such as filtration, centrifugation, or cell sorting. Separated cells, in an embodiment, are lysed before being used as samples in the present invention by one of the methods well known to the skilled artisan. It is to be understood that the sample may be further processed in order to carry out the method of the present invention. In an embodiment, the sample originates from blood. In an embodiment, the sample is a sample of blood or a fraction thereof, in a further embodiment is blood, serum or plasma, in an embodiment is serum or plasma.

The term "subject" as used herein relates to animals, in an embodiment to mammals such as mice, rats, sheep, dogs, cats, horses, monkeys, or cows and, in an embodiment, to humans.

The term "contacting", as used in the context of the methods of the present invention, is understood by the skilled person. In an embodiment, the term relates to bringing a compound, in particular an analyte, into physical contact with a further compound, e.g. a capture agent, and thereby allowing the compound and the further compound to interact. Accordingly, the term "reaction mixture" relates to any mixture contacting a first compound with a second compound, e.g. a capture agent with a sample, allowing said first and second compound to react.

As used herein, the term "capture complex" relates to any, in an embodiment non-covalent, complex comprising at least a capture agent and an analyte as specified elsewhere herein, in an embodiment having a dissociation constant as specified elsewhere herein. Thus, in an embodiment, the analyte is bound to the capture agent in the capture complex as specified herein below. In an embodiment, the capture complex is a specific capture complex, i.e. the capture agent is specifically bound to the analyte in said capture complex.

The term "binding" a first compound to a second compound is understood by the skilled person. In an embodiment, binding relates to an interaction with an affinity of the binding partners high enough to allow for binding the first binding partner to a solid surface without significant leaching of the second binding partner. In an embodiment, binding is binding with a dissociation constant of less than $10^{-5}$ mol/l, in an embodiment less than $10^{-6}$ mol/l, in a further embodiment less than $10^{-7}$ mol/l, in a further embodiment less than $10^{-8}$ mol/l, in a further embodiment less than $10^{-9}$ mol/l. Thus, in an embodiment, the capture complex comprising at least a capture agent and an analyte has a dissociation constant of less than $10^{-5}$ mol/l, in an embodiment less than $10^{-6}$ mol/l, in a further embodiment less than $10^{-7}$ mol/l, in a further embodiment less than $10^{-8}$ mol/l, in a further embodiment less than $10^{-9}$ mol/l. Methods of determining dissociation constants are well known to the skilled artisan and include, e.g., spectroscopic titration methods, surface plasmon resonance measurements, equilibrium dialysis and the like. Binding may be mediated by all kinds of chemical interactions known to the skilled person. In an embodiment, said interactions are non-covalent bonds. As used in this specification, the term "binding", in an embodiment, includes indirect binding, i.e. binding of a first compound to a third compound via a second compound, wherein said first and third compounds, in an embodiment, only interact with the second compound, respectively. In an embodiment, binding is direct binding, i.e. direct interaction of compounds.

In an embodiment, the analyte binds specifically to the capture agent. As the skilled artisan will appreciate, the term "binding specifically", or a grammatical variation thereof, is used to indicate that other compounds, typically biomolecules, present in a sample do not significantly bind to a ligand, in particular a capture agent, of the present invention. In an embodiment, the level of binding of a capture agent to a compound other than the analyte results in a binding affinity which is at most 10% or less, 5% or less, 2% or less, or 1% or less of the affinity to the analyte, respectively.

As used herein, the term "capture agent" relates to a chemical molecule binding to the analyte of the present invention. Thus, in an embodiment, the capture agent is an analyte specific affinity based binder. In an embodiment, the capture agent is an organic molecule or a complex thereof, in a further embodiment, a biological macromolecule, in particular a polypeptide or a complex thereof. In an embodiment, the capture agent is an antibody, an aptamer, an anticalin, or a receptor, or a fragment of one of the aforesaid compounds having the activity as specified above. In an embodiment, the capture agent is a monoclonal antibody.

The capture agent is attached or adapted to be attached to a solid surface. As used herein, the term "solid surface" relates to any suitable solid surface adapted for binding the capture agent of the present invention and adapted for being separated, e.g., by physical means, from a sample. In an embodiment, said solid surface is a surface of a bead, in an embodiment, a microbead, e.g. a magnetic or paramagnetic microbead. In an embodiment, said surface is adapted to improve binding of the capture compound, e.g. by attaching, covalently or non-covalently, molecules binding a substructure of the capture agent. Typical molecules binding a substructure of the capture compound are, e.g. antibodies, streptavidin, complexed Nickel ions, and the like. In a further embodiment, the solid surface binds said capture compound by covalent and/or non-covalent bonds, e.g. by hydrophobic interaction. Thus, in an embodiment, said solid surface is a surface of a multi-cluster plate. In an embodiment, the surface of the multi-cluster plate is pretreated to increase affinity and/or capacity for binding of a capture compound. Suitable pretreatments are known in the art. In a further embodiment, the solid surface is a porous filling of e.g. a pipette tip providing an appropriate surface.

As will be understood by the skilled person, the capture agent may be attached to a solid surface before, simultaneously to, or after contacting said capture agent with an analyte. In an embodiment, the capture agent is attached to a solid surface after contacting said capture agent with an analyte, e.g. by mixing said analyte and said capture agent, followed by binding to a solid surface. As the skilled person will understand, contacting a capture agent with a sample and binding said capture agent to a solid surface allows for specifically separating an analyte bound by said capture agent, if present, from other compounds comprised in said sample. Methods of attaching capture agents, e.g. biological molecules, typically polypeptides, to solid surfaces are well known in the art and include, e.g., binding by hydrophobic interaction, biotinylation and binding via immobilized streptavidin, covalent binding, antibody-antigen interaction, and the like, or a combination of these interactions.

In an embodiment, the capture agent may also be a capture complex. In another embodiment, the capture agent is an antibody, i.e. a capture antibody, in particular a monoclonal antibody. In an embodiment, the capture antibody is covalently coupled to biotin. Thus, in an embodiment, the capture agent is an immobilized capture agent, in an embodiment a capture agent immobilized on a solid surface. In a further embodiment, the capture agent is immobilized on a solid surface via covalent and/or hydrophobic bonds; in a further embodiment, the capture agent is immobilized on a solid surface via a high-affinity interaction, in an embodiment via a streptavidin/biotin interaction.

The term "antibody", as used herein, includes monoclonal antibodies, multispecific antibodies (e.g. bispecific antibodies) formed from at least two intact antibodies, and antibody fragments so long as they exhibit the desired binding activity as specified elsewhere herein. In an embodiment, the antibody is a monoclonal antibody. In an embodiment, the antibody is a full-length antibody or an antibody fragment.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The subunit structures and three-dimensional configurations of different classes of immunoglobulins are well known and described generally in, for example, Abbas et al., Cellular and Mol. Immunology, 4th ed., W.B. Saunders, Co. (2000). An antibody may be part of a larger fusion molecule, formed by covalent or non-covalent association of the antibody with one or more other proteins or peptides.

The terms "full-length antibody," "intact antibody," and "whole antibody" are used herein interchangeably to refer to an antibody in its substantially intact form, not antibody fragments as defined below. The terms particularly refer to an antibody with heavy chains that contain an Fc region. "Antibody derivatives" comprise a portion of an intact antibody, in an embodiment, comprising the antigen-binding region thereof. Thus, an antibody derivative may be an antibody fragment. Examples of antibody derivatives include Fab, Fab', F(ab')2, and Fv fragments; diabodies; linear antibodies; single-chain antibody molecules, nanobodies, and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen. "Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three hypervariable regions (HVRs) of each variable domain interact to define an antigen-binding site. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site. The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 0 404 097; WO 1993/01161; Hudson et al., Nat. Med. 9 (2003) 129-134; and Hollinger et al., PNAS USA 90 (1993) 6444-6448. Triabodies and tetrabodies are also described in Hudson et al., Nat. Med. 9 (2003) 129-134.

The term "monoclonal antibody" as used herein refers to an antibody obtained from a population of substantially homogeneous antibodies, i.e., the individual antibodies comprised in the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds an analyte, wherein the analyte-binding polypeptide sequence was obtained by a process that includes the selection of a single analyte binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target-binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which include different antibodies directed against different determinants (epitopes), each monoclonal antibody of a monoclonal-antibody preparation is directed against a single determinant on an antigen. In addition to their specificity, monoclonal-antibody preparations are advantageous in that they are typically uncontaminated by other immunoglobulins.

Antibodies or derivatives thereof can be obtained by using methods which are described, e.g., in Harlow and Lane "Antibodies, A Laboratory Manual", CSH Press, Cold Spring Harbor, 1988. Monoclonal antibodies can be prepared by the techniques originally described in Köhler and Milstein, Nature 256 (1975), 495, and Galfré, Meth. Enzymol. 73 (1981), 3, which comprise the fusion of mouse myeloma cells to spleen cells derived from immunized mammals.

As used herein, the term "detecting" refers to detecting at least one feature, in an embodiment, a structural and/or quantitative feature, of an analyte, qualitatively or quantitatively. A feature in accordance with the present invention, in an embodiment, is a structural feature of an analyte facilitating detection of the analyte in a sample, e.g. by means of mass spectrometry. In an embodiment, said feature facilitates identification and/or quantification of the analyte. Typical usable features are features facilitating differentiation of said analyte from other chemical compounds present in a sample. In an embodiment, detecting an analyte is establishing whether an analyte is present or absent in the sample at a concentration or amount above the detection limit of the detection method. Methods of establishing a detection limit for a given detection method are known to the skilled person and include, e.g. dilution titration experiments. In a further embodiment, detecting is detecting semi-quantitatively or quantitatively the amount or concentration of an analyte. For quantitative detection, either the absolute or precise amount of the analyte will be detected or the relative amount of the analyte will be detected. The relative amount may be detected in a case were the precise amount can or shall not be detected. In said case, it can be detected whether the amount in which the analyte is present is increased or diminished with respect to a second sample comprising said analyte in a second, in an embodiment pre-determined, amount.

In an embodiment, detecting an analyte comprises separating at least one fragment of said analyte produced by cleaving at least one covalent bond within said analyte and/or within said capture agent from further compounds. Methods of separating chemical compounds from each other, e.g. separating individual peptides, are known in the art and include extraction, precipitation, centrifugation, chromatography, and the like. In an embodiment, separating at least one fragment of said analyte is achieved by chromatography, in an embodiment by liquid chromatography (LC).

As will be understood by the skilled person, the method selected for identifying and/or quantifying an analyte will depend on the assay format chosen and on the analyte or fragment thereof to be detected. Suitable methods are, in principle, known to the skilled person. In an embodiment, in particular in case the analyte is a polypeptide, the assay is an immunological assay, wherein the analyte is bound to a capture compound, which may be attached to a solid surface, by immunological means. In an embodiment the amount of analyte captured is detected by binding of a detector compound, e.g. a labeled second antibody, to said captured analyte. In an embodiment, the capture and/or detector compound is an antibody and the assay is a sandwich immunoassay.

In an embodiment, the analyte is identified and/or quantified by a method comprising mass spectrometry (MS). Thus, in an embodiment, detecting the analyte comprises detecting said analyte or fragments thereof by mass spectrometry (MS), in an embodiment by LC-coupled mass spectrometry (LC-MS). In a further embodiment, in particular in case the analyte is a polypeptide, detecting comprises detecting the analyte or fragments thereof by multiple reaction monitoring (MRM)-MS, in an embodiment MRM-LC-MS. In an embodiment, detecting comprises MS and fragments of the analyte are detected. In an embodiment, the analyte is PSA, the at least one covalent bond is cleaved with Trypsin and detecting the analyte PSA comprises detecting at least one tryptic fragment of PSA, in an embodiment comprises detecting at least one fragment selected from the group consisting of fragments having a molecular mass of 756.5 Da, 463.2 Da, 609.3 Da, and 1271.7 Da.

The method of the present invention comprises detecting an analyte or fragment thereof, as specified above. As will be understood by the skilled person, the method may further comprise detecting further fragments of the analyte and even further analytes, in particular in case MS is used for detection.

In an embodiment, the method for detecting an analyte comprises further steps of modifying said analyte. As used herein, the term "modifying" an analyte relates to causing a structural change in the analyte to occur. In an embodiment, a structural change is an isomerization or an addition or removal of a part of the structure of the analyte. In an embodiment, modifying is derivatizing an analyte, i.e. adding a chemical side chain to the analyte. In a further embodiment, modifying is cleaving, in an embodiment hydrolyzing, non-backbone covalent bonds, in particular removing a side chain modification, e.g. in a polypeptide. In an embodiment, a further step of cleaving, in an embodiment hydrolyzing, non-backbone covalent bonds is performed before the step of cleaving at least one covalent bond within said analyte bound to said capture agent and/or within said capture agent. In a further embodiment, at least one further step of hydrolyzing non-backbone covalent bonds is performed while said analyte is bound to said capture agent. Thus, in an embodiment, at least one further step of hydrolyzing non-backbone covalent bonds is performed on a capture complex. In an embodiment, the least one further step of hydrolyzing non-backbone covalent bonds comprises a deglycosylation step, in an embodiment enzymatic deglycosylation of said analyte bound to said capture agent.

In a further embodiment, the least one further step of hydrolyzing non-backbone covalent bonds comprises the further step of contacting said analyte with a hydrolase (EC 3), in a further embodiment with a glycosylase (EC 3.2), in a further embodiment with a glycosidase (EC 3.2.1), in a further embodiment with an exo-alpha-Sialidase (EC 3.2.1.18), an endo-alpha-Sialidase (EC 3.2.1.129), an alpha-Galactosidase (EC 3.2.1.22), a beta-Galactosidase (EC 3.2.1.23), an alpha-Mannosidase (EC 3.2.1.24), a mannosyl-oligosaccharide 1,2-alpha-mannosidase (EC 3.2.1.113), a mannosyl-oligosaccharide 1,3-1,6-alpha-mannosidase (EC 3.2.1.114), a beta-Mannosidase (EC 3.2.1.25), an alpha-N-acetylgalactosaminidase (EC 3.2.1.49), a beta-N-acetylgalactosaminidase (EC 3.2.1.53), an alpha-L-fucosidase (EC 3.2.1.51), a 1,2-alpha-L-fucosidase (EC 3.2.1.63), a 1,3-alpha-L-fucosidase (EC 3.2.1.111), a 1,6-alpha-L-fucosidase (EC 3.2.1.127), a beta-L-N-Acetylhexosaminidase (EC 3.2.1.52), an endo-alpha-Sialidase (EC 3.2.1.129) and/or a mannosyl-glycoprotein endo-beta-N-acetylglucosamidase (EC 3.2.1.96), in a further embodiment with endoglycosidase Endo F3 (endo-beta-N-acetylglucosaminidase F3, e.g. from *Elizabethkingia miricola*) or EndoS2 from *Streptococcus pyogenes*, which is, e.g. marketed as GlycINATOR®. In a further embodiment, the least one further step of hydrolyzing non-backbone covalent bonds comprises the further step of contacting said analyte with endoglycosidase Endo F3.

In a further embodiment, the least one further step of hydrolyzing non-backbone covalent bonds comprises the further step of contacting said analyte with an enzyme that acts on carbon-nitrogen bonds other than peptide bonds (EC 3.5), in a further embodiment with an enzyme that acts on linear amides (EC 3.5.1), in a further embodiment with a peptide-N4-(N-acetyl-beta-glucosaminyl) asparagine amidase, in a further embodiment with endoglycosidase PNGase F (Peptide-N-Glycosidase F, e.g. from *Flavobacterium meningosepticum*). In a further embodiment, the least one further step of hydrolyzing non-backbone covalent bonds comprises the further step of contacting said analyte with endoglycosidase PNGase F. The skilled person is able to select an appropriate hydrolase and appropriate hydrolysis conditions suitable for modifying the analyte, e.g. by incubating the analyte in the presence of a hydrolase as specified herein above and testing whether the desired modification has occurred. The skilled person is also able to select suitable reaction conditions, e.g. from literature, from a package leaflet, or by determining suitable conditions experimentally.

As will be understood by the skilled person, the analyte may be contacted with more than one of the aforesaid enzymes hydrolyzing non-backbone covalent bonds, in particular with at least two, at least three, or at least four enzymes hydrolyzing non-backbone covalent bonds. In an embodiment, contacting the analyte with more than one enzyme hydrolyzing non-backbone covalent bonds is performed sequentially; in a further embodiment, contacting the analyte with more than one enzyme hydrolyzing non-backbone covalent bonds is performed simultaneously, i.e. by contacting the analyte with at least two or more of said enzymes hydrolyzing non-backbone covalent bonds at the same time. The skilled person knows how to select hydrolysis conditions in such case. The skilled person, however, is aware that not all combinations of said enzymes may be compatible e.g. for different requirements regarding reaction temperature, pH, cofactors, or ions and, in case of incompatibility, will consider sequential treatment.

Advantageously, it was found in the work underlying the present invention that fragments of an analyte can be obtained from an analyte in a capture complex, providing the possibility to obtain an indication on the identity and/or amount of an analyte in a sample without having to apply the harsh elution conditions used in the art. The eluate obtained can, e.g., be used directly as sample for LC, in particular HPLC. Moreover, it was found that deglycosylation of a polypeptide may be more efficient while said polypeptide is attached to a solid surface.

The definitions made above apply mutatis mutandis to the following. Additional definitions and explanations made further below also apply for all embodiments described in this specification mutatis mutandis.

Further, the present invention relates to a kit comprising i) a capture agent binding, in an embodiment specifically binding, to an analyte; and ii) an agent cleaving at least one covalent bond within said analyte and/or within said capture agent.

The term "kit", as used herein, refers to a collection of the aforementioned compounds, means or reagents of the present invention which may or may not be packaged together. The components of the kit may be comprised by separate vials (i.e. as a kit of separate parts) or two or more components may be provided in a single vial. In an embodiment, the capture agent and the agent cleaving at least one covalent bond are comprised by separate vials. Moreover, it is to be understood that the kit of the present invention, in an embodiment, is to be used for practicing the methods referred to herein above. It is, in an embodiment, envisaged that all components are provided in a ready-to-use manner for practicing the methods referred to above. Further, the kit, in an embodiment, contains instructions for carrying out said methods. The instructions can be provided by a user's manual in paper- or electronic form. In addition, the manual may comprise instructions for interpreting the results obtained when carrying out the aforementioned methods using the kit of the present invention. In an embodiment, the kit further comprises a buffer, in particular an elution buffer for eluting the analyte or fragment thereof from a solid support. In an embodiment, the kit further comprises a solid support, e.g. in the form of beads or matrix-filled pipette tips. Further embodiments of solid surfaces are described herein above. In an embodiment, the kit further comprises an additional agent modifying the analyte, in an embodiment an agent cleaving at least one non-backbone covalent bond of said analyte, in particular an enzyme, e.g. a glycosidase, in an embodiment a glycosidase as specified herein above. In an embodiment, the agent cleaving at least one non-backbone covalent bond is a glycosidase, in an embodiment is an endoglycosidase, in a further embodiment is Endo F3.

A person skilled in the art is able to generate a specific binding agent, e.g. an antibody, in particular a monoclonal antibody, binding to a target; or to select a binding agent known in the art, e.g. a commercially available antibody, specific for an antigen of interest to be captured. Appropriate embodiments of capture compounds have been described herein above. Accordingly, in an embodiment, the capture compound is an antibody or fragment thereof. Appropriate embodiments of agents cleaving at least one covalent bond within said analyte and/or within said capture agent are also described herein above. Thus, in an embodiment, the agent cleaving at least one covalent bond within said analyte and/or within said capture agent is a protease, in an embodiment is an endopeptidase, in a further embodiment is Trypsin.

The present invention further relates to a use of an enzyme for releasing fragments of an analyte for detecting said analyte, wherein said analyte is bound to a solid surface via a capture agent.

In an embodiment, the use is a use of the method for detecting an analyte as specified herein above. In an embodiment, said enzyme is a hydrolase, in a further embodiment, the enzyme is a protease and/or a glycosidase as specified herein above.

The present invention also relates to a method for diagnosing disease, comprising the steps of the method for detecting an analyte as specified herein above and the further step of comparing an amount of analyte determined to a reference, thereby diagnosing disease.

The method for diagnosing disease of the present invention, in an embodiment, is an in vitro method. Moreover, it may comprise steps in addition to those explicitly mentioned above. For example, further steps may relate, e.g., to obtaining a sample from a subject for step a), or structurally modifying, e.g. derivatizing the at least one fragment of the analyte after step b). Moreover, one or more of said steps may be performed by automated equipment.

The method for diagnosing disease of the present invention is, in principle, applicable for the diagnosis of any disease in which at least one analyte is present in a sample of a subject at a concentration deviating from the concentration of said analyte in a subject not suffering from said disease, and wherein said analyte binds to a capture agent. Thus, in an embodiment, the analyte is a biological macromolecule as specified herein above. In an embodiment, the analyte is a polypeptide. In a further embodiment, the analyte is PSA and said disease is prostate cancer.

The term "diagnosing", as used herein, refers to assessing the probability according to which a subject is suffering from a disease or condition or is at risk of developing a disease or condition. Accordingly, the method provides an aid for diagnosis since it might be necessary to further strengthen or confirm said diagnosis by, e.g., a medical practitioner. In particular, as will be understood by those skilled in the art, such an assessment, although preferred to be, may usually not be correct for 100% of the subjects to be diagnosed. The term, in an embodiment, requires that a statistically significant portion of subjects can be identified as suffering from the disease or as having a predisposition therefor. Whether a portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 50%, at least 60%, at least 70%, at least 80%, at least 90%, at least 95%. The p-values are, in an embodiment, 0.2, 0.1, 0.05. It will be understood, moreover, that the methods of the present invention essentially provide an aid for diagnosis and may be included into or supplemented by other diagnostic measures. Diagnosing according to the present invention includes monitoring, confirmation, and classification of the relevant disease or its symptoms. Monitoring relates to keeping track of an already diagnosed disease, or a complication, e.g. to analyze the progression or regression of the disease, the influence of a particular treatment on the progression of disease or complications arising during the disease period or after successful treatment of the disease. Confirmation relates to the strengthening or substantiating a diagnosis already established using other indicators or markers. Classification relates to allocating the diagnosis according to the strength or kind of symptoms into different classes, e.g. the stages for prostate carcinomas. Being at risk as used herein means that a subject has not yet developed the disease or condition but, nevertheless, will develop it in the future with a certain likelihood. Diagnosis of a predisposition may sometimes be referred to as prediction of the likelihood that a subject will develop the disease.

The term "reference" refers to amounts or values representing them, i.e. data of characteristic features of the an analyte, which can be correlated to the presence or absence of a disease or condition. Such a reference is, in an embodiment, obtained from a sample of a subject or group of subjects known to suffer from the disease to be diagnosed. The reference can, e.g., be the average or mean obtained from a group of such samples. The reference may be obtained by applying the method of the present invention. Alternatively, a reference may be obtained from sample of a subject or a group of subjects known not to suffer from the disease to be diagnosed. Moreover, the reference, may be a calculated reference, e.g. the average or median, for the relative or absolute amount of an analyte of a representative population of individuals which are apparently healthy. The absolute or relative amounts of the analyte of said individuals of the population can be determined according to the present invention. How to calculate a suitable reference value, in an embodiment, the average or median, is well known in the art. The population of subjects referred to before shall comprise a plurality of subjects, in an embodiment at least 5, 10, 50, 100, 1,000 or 10,000 subjects. It is to be understood that the subject to be diagnosed by the method of the present invention and the subjects of the said plurality of subjects are, in an embodiment, of the same species. The skilled person knows how to establish a reference value, which may be a cut-off vale, an upper limit of normal, a median or average, a reference range, or the like.

In view of the above, the following embodiments are particularly envisaged:

1. A method for detecting an analyte comprising
a) contacting said analyte, a capture agent and a solid surface to form a capture complex attached to a solid surface,
b) cleaving at least one covalent bond within said analyte and/or within said capture agent comprised in said capture complex and, thereby, releasing said analyte or a fragment thereof from said capture complex, and
c) detecting said analyte or fragment thereof and, thereby, detecting said analyte.

2. The method of embodiment 1, wherein said analyte is a macromolecule, in an embodiment a biological macromolecule.

3. The method of embodiment 1 or 2, wherein said analyte is a polynucleotide or a polypeptide, in an embodiment is a polypeptide.

4. The method of any one of embodiments 1 to 3, wherein said analyte is PSA.

5. The method of any one of embodiments 1 to 4, wherein said analyte is comprised in a sample, in an embodiment in a sample of a subject.

6. The method of any one of embodiments 1 to 5, wherein said sample is a sample of blood or a fraction thereof, in an embodiment is blood, serum or plasma, in an embodiment is serum or plasma.

7. The method of any one of embodiments 1 to 6, wherein said capture agent is an agent specifically binding to said analyte.

8. The method of any one of embodiments 1 to 7, wherein said capture agent is a macromolecule, in an embodiment is a biological macromolecule, in a further embodiment is an antibody, or a derivative thereof, in a further embodiment is an antibody or a derivative thereof.

9. The method of any one of embodiments 1 to 8, wherein said capture agent is attached to a solid surface simultaneously to contacting said capture agent with said analyte.

10. The method of any one of embodiments 1 to 9, wherein said capture agent is immobilized on a solid surface via covalent and/or hydrophobic bonds.

11. The method of any one of embodiments 1 to 10, wherein said capture agent is immobilized on a solid surface via a high-affinity interaction, in an embodiment via a streptavidin/biotin interaction.

12. The method of any one of embodiments 1 to 11, wherein said cleaving at least one covalent bond comprises hydrolyzing, in an embodiment enzymatically hydrolyzing, at least one covalent bond within said analyte.

13. The method of any one of embodiments 1 to 12, wherein cleaving at least one covalent bond within said analyte is cleaving at least one backbone covalent bond or is cleaving at least one non-backbone covalent bond.

14. The method of any one of embodiments 1 to 13, wherein said analyte is a polypeptide and wherein cleaving at least one covalent bond within said analyte comprises hydrolyzing, in an embodiment enzymatically hydrolyzing, at least one peptide bond within said analyte.

15. The method of any one of embodiments 1 to 14, wherein said cleaving at least one covalent bond within said analyte comprises contacting said analyte with at least one protease, in an embodiment an endopeptidase, in a further embodiment Trypsin.

16. The method of any one of embodiments 1 to 15, wherein said at least one fragment of said analyte is a specific fragment of said analyte.

17. The method of any one of embodiments 1 to 16, wherein said method comprises further steps of modifying said analyte.

18. The method of any one of embodiments 1 to 17, wherein said method comprises at least one further step of derivatizing said analyte or a fragment thereof.

19. The method of any one of embodiments 1 to 18, wherein said method comprises at least one step of hydrolyzing non-backbone covalent bonds, in an embodiment at least one further step of hydrolyzing non-backbone covalent bonds.

20. The method of any one of embodiments 1 to 19, wherein said at least one further step of hydrolyzing non-backbone covalent bonds is performed before the step of cleaving at least one backbone covalent bond within said analyte bound to said capture agent and/or within said capture agent.

21. The method of any one of embodiments 1 to 20, wherein said at least one step or further step of hydrolyzing non-backbone covalent bonds is performed while said analyte is bound to said capture agent.

22. The method of any one of embodiments 1 to 21, wherein said method comprises at least one step of deglycosylation, in an embodiment enzymatic deglycosylation, of said analyte bound to said capture agent; in a further embodiment comprises at least one further step of deglycosylation, in an embodiment enzymatic deglycosylation, of said analyte bound to said capture agent.

23. The method of any one of embodiments 1 to 22, wherein said method comprises the step of contacting said analyte with an endoglycosidase, in an embodiment with Endo F3; in a further embodiment comprises the further step of contacting said analyte with an endoglycosidase, in an embodiment with Endo F3.

24. The method of any one of embodiments 1 to 23, wherein said detecting comprises separating said at least one fragment of said analyte from further compounds, in an embodiment by chromatography, in a further embodiment by liquid chromatography (LC).

25. The method of any one of embodiments 1 to 24, wherein said detecting comprises detecting said analyte or fragments thereof by mass spectrometry (MS), in an embodiment LC-coupled mass spectrometry (LC-MS).

26. The method of any one of embodiments 1 to 25, wherein said detecting comprises detecting said analyte or fragments thereof by multiple reaction monitoring (MRM)-MS, in an embodiment MRM-LC-MS.

27. A kit comprising i) a capture agent binding, in an embodiment specifically binding, to an analyte; and ii) an agent cleaving at least one covalent bond within said analyte and/or within said capture agent.

28. The kit of embodiment 27, wherein said capture agent is an analyte specific affinity based binder, in an embodiment selected from the list consisting of an antibody, in particular a polyclonal or monoclonal antibody, an aptamer, and a receptor.

29. The kit of embodiment 27 or 28, wherein said capture agent is an antibody or fragment thereof.

30. The kit of any one of embodiments 27 to 29, wherein said agent cleaving at least one covalent bond within said analyte and/or within said capture agent is a protease, in an embodiment is an endopeptidase, in a further embodiment is Trypsin.

31. The kit of any one of embodiments 27 to 30, wherein said kit further comprises at least one solid support.

32. The kit of any one of embodiments 27 to 31, wherein said kit further comprises an agent cleaving at least one non-backbone covalent bond of said analyte, in an embodiment a glycosidase, in an embodiment is an endoglycosidase, in a further embodiment is Endo F3.

33. The kit of any one of embodiments 27 to 32, wherein said agent cleaving at least one covalent bond within said analyte and/or within said capture agent is an agent cleaving at least one non-backbone covalent bond, in an embodiment is a glycosidase, in a further embodiment is an endoglycosidase, in a further embodiment is Endo F3.

34. Use of an enzyme for releasing fragments of an analyte for detecting said analyte, wherein said analyte is bound to a solid surface via a capture agent.

35. The use of embodiment 34, wherein said use is a use of the method of any one of embodiments 1 to 26.

36. A method for diagnosing disease, comprising the steps of any one of embodiments 1 to 26 and the further steps of comparing an amount of analyte determined to a reference, thereby diagnosing disease.

37. The method of embodiment 36, wherein said analyte is PSA and wherein said disease is prostate cancer.

All references cited in this specification are herewith incorporated by reference with respect to their entire disclosure content and the disclosure content specifically mentioned in this specification.

The following Examples shall merely illustrate the invention. They shall not be construed, whatsoever, to limit the scope of the invention.

Example 1: Materials 1.1 Immune Enrichment

Phosphate buffered saline (PBS, Cat.-Nr. P4417) was from Sigma. The biotinylated antibody fragment MAK<PSA>M-36-Fab-Bi mono, which is also commercially available as a component of the Reagent 1 (R1) of the Roche Total PSA Elecsys Test/Assay (Roche order number 04641655190), was produced in-house (Lot Bg01MP) according to standard methods as described e.g. in the EZ-Link® Sulfo-NHS-LC-Biotinylation Kit (Pierce). Streptavidin packed pipette tips MSIA D.A.R.T.'s, Streptavidin (Cat.-Nr. 991STR11), Finnpipette™ Novus i Multichannel Electronic and pipette holder (Cat.-Nr. 991SP12) were from ThermoScientific. The PSA CalSet II (Ref. 04485220190, Lot 180 622-02) was from Roche. Deepwell Plate 96/500 µL Protein LoBind (Cat.-No. 951032107) was from Eppendorf.

1.2 Endo-Deglycosylation and Digestion

Trifluoroacetic acid ULC/MS (TFA, Cat.-Nr. 0020234131BS, Lot 1048611) glacial acetic acid (Cas. 64-19-7, Lot 704681) were from Biosolve. Sodium acetate (Cat.-Nr.1.06268.1000, Lot A0195768119) was from Merck, Ammoniumbicarbonate (ABC, Cas. 1066-33-7, Lot 0902801004) was from J.T. Baker, Trypsin (Cat.-Nr. T6567, Lot SLBH0629V) was obtained from Sigma, and Endo F3 (Cat.-Nr. E-EF03, Lot 902.1A) from QA-Bio. Incubation at 37° C. was performed in a Thermomixer C from Eppendorf or incubator Type B 6030 from Heraeus instruments was used. Samples were dried in a Concentrator 5301 from Eppendorf.

1.3 LC-MS

Acetonitrile ULC/MS (ACN, Cas. 75-05-8, Lot 1076121) and formic acid 99% ULC/MS (Cat.-Nr. 0006914143BS, Lot 1061561) were from Biosolve. The chromatography system was an Infinity 1290 HPLC from Agilent, comprising a binary pump (G4220A), a column oven (G1316C), an autosampler (G4226A) and a thermostat (G1330B). LC-separation was performed using an Xbridge Amide column (130A, 3.5 µm, 2.1×100 mm, Part Nr. 186004860, Serial Nr. 01253526417909, Lot 0125352641) from Waters. The MS was a QTRAP 6500 with a Turbo V™ ion source from AB Sciex.

Example 2: Methods 2.1 Preparation of Samples, Buffers, and Solutions:

Water was purified in a Milli-Q plus device from pure Aqua. Lyophilized PSA from a Calibrator set was dissolved in 10000 µl $H_2O$, creating a serum solution with a PSA concentration of approximately 60 ng/ml. 10 mM PBS was made by dissolving a PBS tablet in 200 ml $H_2O$. 4995 µl of 10 mM PBS-buffers were mixed with 5 µl TWEEN® 20. A 0.01 µg/µl MAK<PSA>M-36 solution was made by diluting 60 MAK<PSA>M-36-Fab-Bi mono (5.54 mg/ml) with 3316 µl 10 mM PBS-buffer. 100 mM ABC-Puffer (pH 7.8) was made by dissolving 393 mg ABC in 50 ml $H_2O$. 409 mg sodium acetate were dissolved in 30 ml $H_2O$, adjusted to pH 4.5 with glacial acetic acid and filled up to 50 ml with $H_2O$, creating a 100 mM sodium acetate buffer (pH 4.5). 20 µg lyophilized Trypsin was dissolved in 100 µl 100 mM ABC-buffer. 30 µl of the Trypsin solution thus created were diluted with 30 µl 100 mM ABC-Puffer, such that a 0.2 µg/µl and 0.1 µg/µl Trypsin solution were obtained. Eluent A was produced by adding 1 ml formic acid to 1000 ml $H_2O$. Eluent B was produced by adding 1 ml formic acid to 1000 ml ACN. The elution buffer was prepared by mixing 40 ml ACN, 60 ml $H_2O$ and 400 µl TFA.

2.2 Sample Treatment 2.2.1 Immune Enrichment

Into a Deepwell-Plate 96, the volumes indicated in Table 1, columns 2-3 were pipetted for steps 1 to 6. Thereafter, the volumes indicated in Table 1, column 4 were automatically pipetted up and down the Streptavidin-packaged pipette tips. Pipetting was repeated for the number of times indicated in Table 1, column 5.

TABLE 1

| | Immune enrichment | | | |
|---|---|---|---|---|
| Step | Solution | Volume in Deepwell-Plate [µl] | Pipetted Volume [µl] | Number of repetitions |
| 1 | 10 mM PBS-buffer | 200 | 175 | 20 |
| 2 | 0.01 µg/µl MAK < PSA > M-36 | 125 | 100 | 400 |
| 3 | 10 mM PBS-buffer | 200 | 175 | 20 |
| 4 | 60 ng/ml total PSA Cal2 | 100 | 75 | 1000 |
| 5 | 10 mM PBS-buffer with 0.1% Tween | 200 | 175 | 20 |
| 6 | $H_2O$ | 200 | 175 | 20 |

2.2.2 Endo-Deglycosylation and Digestion

After immune enrichment according to 2.2.1. (forming of capture complexes), endo-deglycosylation, followed by enzymatic proteolysis was performed directly in the Streptavidin-packaged pipette tips or in solution as follows:

Enzyme Treatment in Solution

Figure 1B:
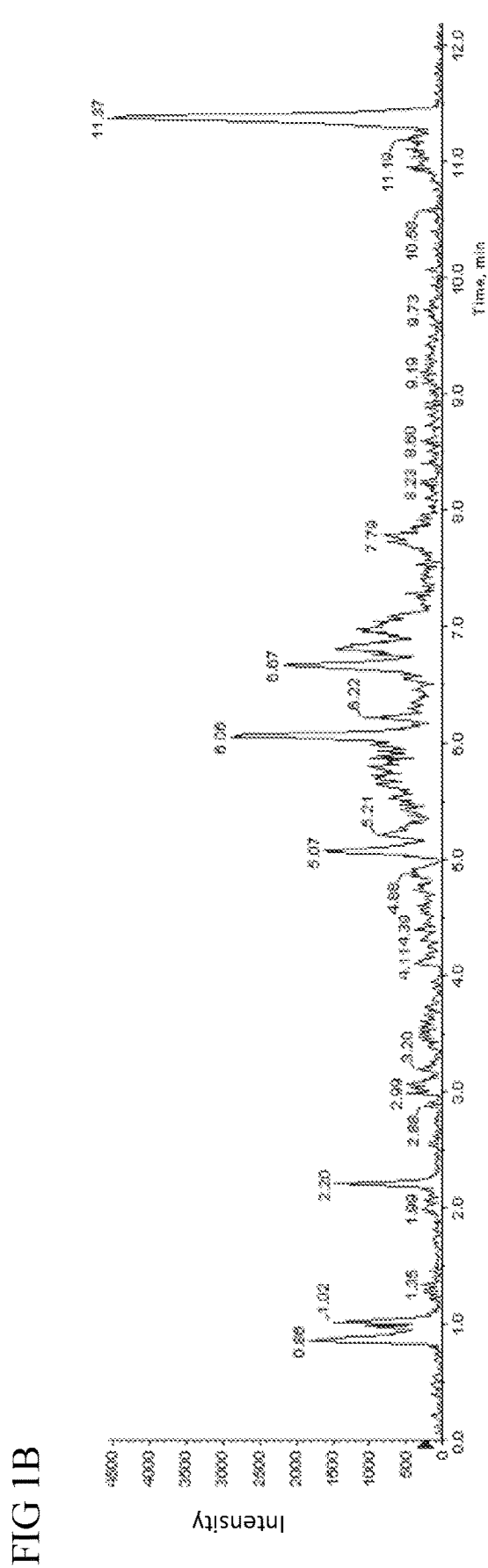
FIG. 1B: Extracted-Ion Current (XIC) chromatogram showing detection of fucosylated PSA glycopetide (N(+GlcNAc+Fuc)K) produced by deglycosylation and protease treatment in solution as described in the Examples. A first fragment with an elution time of 8.15 min is not generated; x-axis: elution time in min, y-axis: intensity in counts per second (cps).
Figure 1C:
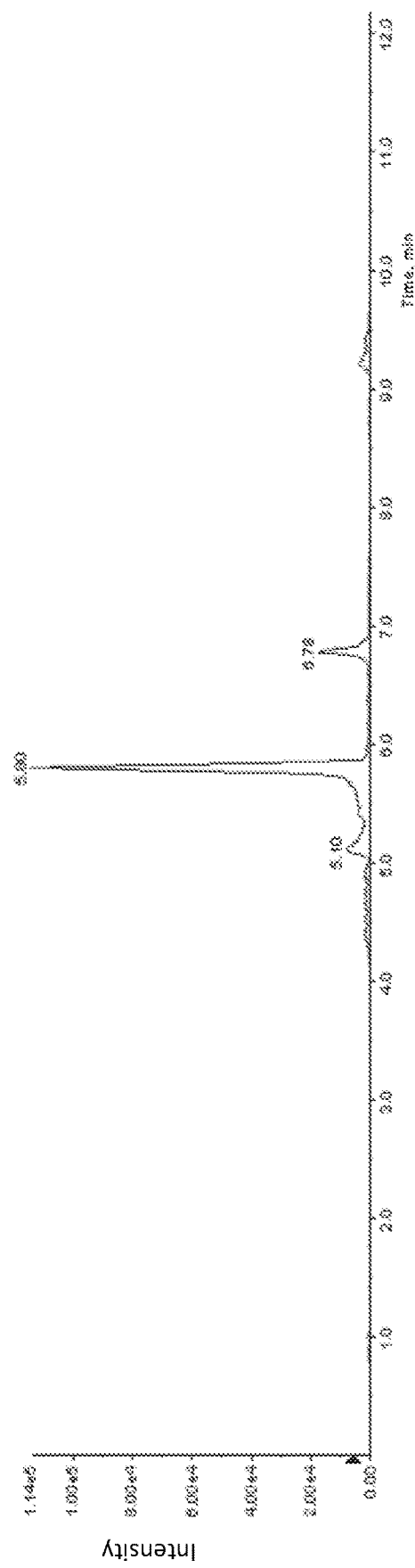
FIG. 1C: Extracted-Ion Current (XIC) chromatogram showing detection of total PSA peptide (LSEPAELTDAVK, SEQ ID NO:1) produced by deglycosylation and protease treatment in solution as described in the Examples. A second fragment with an elution time of 5.80 min is generated by proteolysis alone, independently of deglycosylation; x-axis: elution time in min, y-axis: intensity in counts per second (cps).

The analyte was eluted from the Streptavidin-packaged pipette tips using 25 µl elution buffer by manually pipetting up and down 10 µl of the elution buffer 20 times. After this, 20 µl 100 mM ABC-Puffer (pH 7.8), followed by 2 µl Endo F3 (5 units/ml) were added and agitated at 37° C. for 21 h at 1000 rpm. Following, 40 µl 100 mM ABC-Puffer (pH 7.8) and 5 µl Trypsin (0.2 µg/µl) were added and agitated at 37° C. for 21 h at 1000 rpm. Following, the sample was dried completely in vacuo (45° C., 2 h). The dried residue was dissolved in 25 µl Eluent B with 40% Eluent A (v/v) and transferred into a glass vial with microinsert. A representative example of an analysis of the result of this treatment is shown in FIG. 1; only the fragment with an elution time of approx. 5.80 min, which is diagnostic for PSA, was detected.

Enzyme Treatment Directly on the Pipette Tip

Figure 2A:
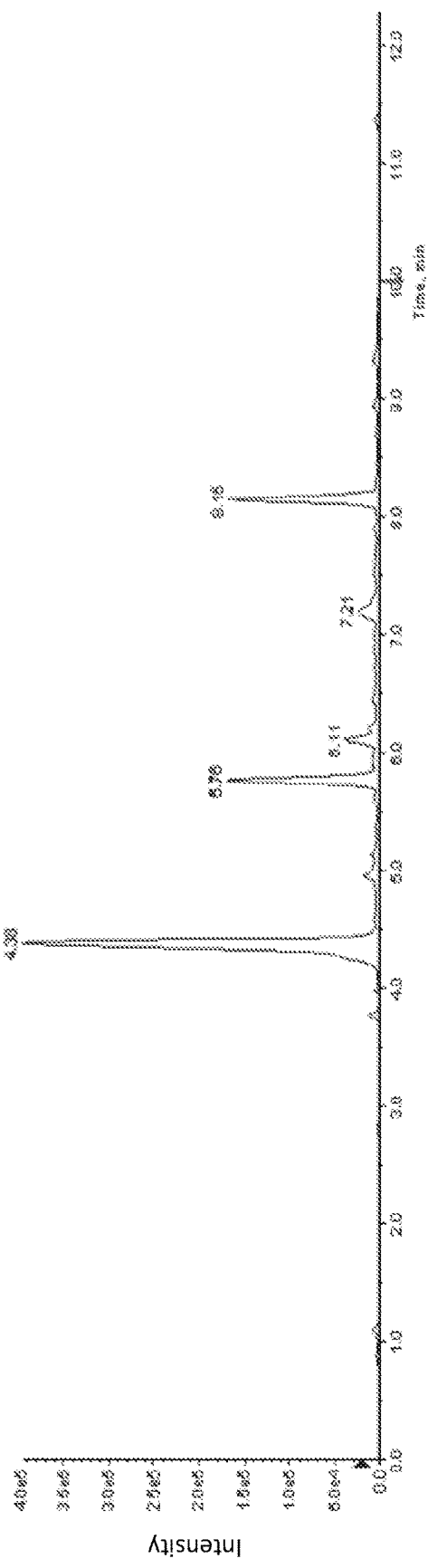
FIG. 2A: Reconstructed Total Ion Current Chromatogram (RTICC) showing detection of fragments of PSA produced by deglycosylation and protease treatment directly on the pipette tip as indicated in the Examples. A first fragment with an elution time of 8.15 min and a second fragment with an elution time of 5.80 min is generated. x-axis: elution time in min, y-axis: intensity in counts per second (cps).
Figure 2B:
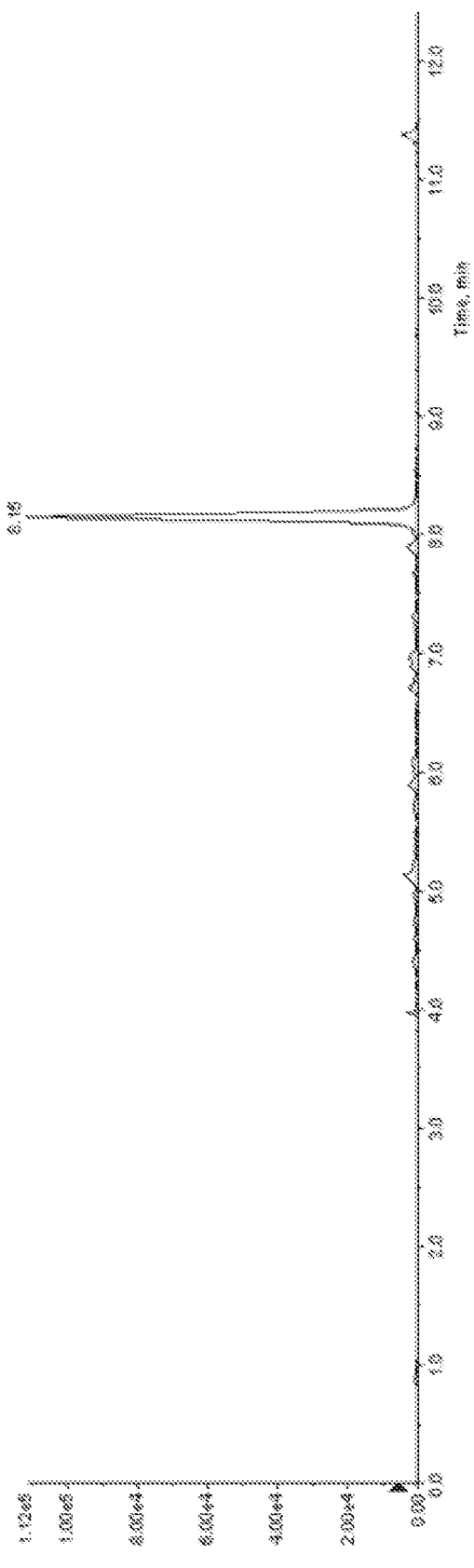
FIG. 2B: Extracted-Ion Current (XIC) chromatogram showing detection of a fucosylated PSA glycopetide (N(+GlcNAc+Fuc)K) produced by deglycosylation and protease treatment directly on the pipette tip as indicated in the Examples. A first fragment with an elution time of 8.15 min is generated; x-axis: elution time in min, y-axis: intensity in counts per second (cps).
Figure 2C:
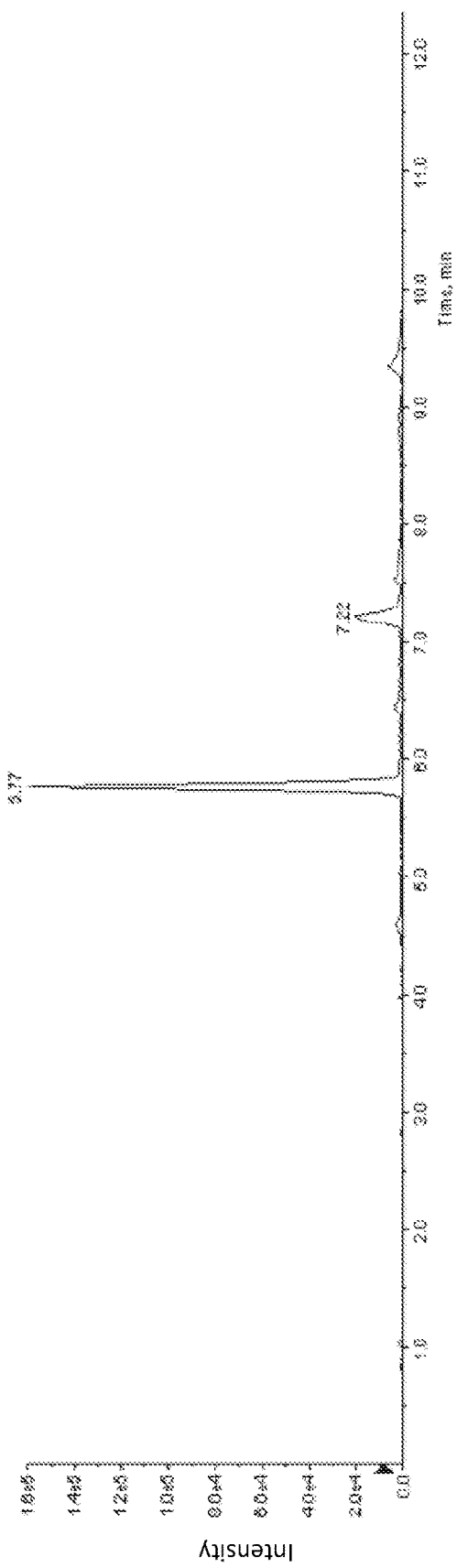
FIG. 2C: Extracted-Ion Current (XIC) chromatogram showing detection of a total PSA peptide (LSEPAELTDAVK, SEQ ID NO:1) produced by deglycosylation and protease treatment directly on the pipette tip as indicated in the Examples. A a second fragment with an elution time of 5.80 min is generated. x-axis: elution time in min, y-axis: intensity in counts per second (cps).

Into a 0.5 ml Lo-Bind tube, 8 µl 100 mM sodium acetate (pH 4.5) and 2 µl Endo F3 (5 units/ml) were pipetted. The resulting solution was manually and completely drawn into the Streptavidin-packaged pipette tip. The pipette tip was left standing in the Lo-Bind tube and was incubated at 37° C. for 21 h in an incubator. Following, the pipette tip was washed with 200 μl 100 mM ABC-Puffer (pH 7.8) by automatically pipetting up and down 175 μl of the buffer 20 times. Following, 10 μl Trypsin (0.1 μg/μl) were pipetted into a glass vial with microinsert and were drawn into the pipette tip manually and completely. The pipette tip was left standing in the glass vial and was incubated at 37° C. for 21 h in an incubator. Following, the contents of the pipette tip was transferred completely into the microinsert and the pipette tip was washed with 20 μl Eluent B with 10% Eluent A by pipetting up and down 10 μl of the solution 20 times manually. The wash solution was combined with the contents of the microinsert. A representative example of an analysis of the result of this treatment is shown in FIG. 2; the fragment with an elution time of approx. 5.80 min and an additional fragment at an elution time of approx. 8.15 min, both of which are diagnostic for PSA, were detected.

Example 3: LC-MS 3.1 HPLC Conditions

Flow rate was 0.3 ml/min and the proportion of Eluent A was 10% at the start of the gradient; within 10 min, the proportion of Eluent A was increased to 50%. After further 0.1 min, the proportion of Eluent A as increased to 70% and maintained for 3.9 min. Following, the proportion of Eluent A was decreased within 0.1 min to 10% and maintained for further 5.9 min. The injection volume was 20 μl and the temperature of the column oven was 50° C.

3.2 MS Conditions

The MS device was tuned and calibrated using Polypropylenglycol, ES Tuning Mix and Tuning Mix Solvent from AB Sciex according to manufacturer's instructions. Resolution of Q1 and Q3 was adjusted at a scan speed of 10 Da/s to 0.7±0.1 amu peak full width at half maximum. Measurements were performed in positive ionization mode. Source parameters are summarized in Table 2, and analyte specific parameters are summarized in Table 3. Waiting time between MRM-transitions was 5 ms.

TABLE 2

| Source parameters | |
| --- | --- |
| Curtain Gas [psi] | 30 |
| Collision Gas [psi] | 12 |
| Ion Spray Voltage [volts] | 4500 |
| Temperature [° C.] | 450 |
| Ion Source Gas 1 [psi] | 50 |
| Ion Source Gas 2 [psi] | 70 |

TABLE 3

| Analyte specific parameters | | | | | | | |
| --- | --- | --- | --- | --- | --- | --- | --- |
| Peptide | Q1 [Da] | Q3 [Da] | Dwell time [ms] | Declustering Potential [volts] | Entrance Potential [volts] | Collision Energy [volts] | Cell Exit Potential [volts] |
| NK + GlcNAc | 464.240 | 261.100 | 100.0 | 75.000 | 10.000 | 27.000 | 15.000 |
| NK + GlcNAc + Fuc (1) | 610.290 | 464.300 | 100.0 | 110.000 | 10.000 | 30.000 | 6.000 |
| NK + GlcNAc + Fuc (2) | 610.290 | 261.100 | 100.0 | 100.000 | 10.000 | 39.000 | 11.000 |
| LSEPAELTDAVK (1) | 636.840 | 472.200 | 100.0 | 25.000 | 10.000 | 24.000 | 15.000 |
| LSEPAELTDAVK (2) | 636.840 | 183.100 | 100.0 | 50.000 | 10.000 | 30.000 | 5.000 |
| SVILLGR (1) | 379.250 | 571.200 | 100.0 | 25.000 | 10.000 | 15.000 | 11.000 |
| SVILLGR (2) | 379.250 | 458.300 | 100.0 | 35.000 | 10.000 | 15.000 | 11.000 |

Example 4: Data Acquisition and Analysis

Instrument control, data acquisition and processing, as well as analysis was performed using Analyst Software 1.6.2 from AB Sciex, using a Smoothing Width Factor of 3. Peak integration was performed automatically with the IntelliQuan Integration Algorithm.

The invention claimed is:

1. A method for detecting an analyte comprising
   a) contacting said analyte, a capture agent and a solid surface to form a capture complex attached to a solid surface,
   b) cleaving at least one covalent bond within said analyte and/or within said capture agent comprised in said capture complex and, thereby, releasing said analyte or a fragment thereof from said capture complex, and
   c) detecting said analyte or fragment thereof and, thereby, detecting said analyte, wherein said capture agent is attached to said solid surface simultaneously to contacting said capture agent with said analyte, and wherein said method comprises at least one further step of deglycosylation of said analyte bound to said capture agent.

2. The method of claim 1, wherein said analyte is a polypeptide.

3. The method of claim 1, wherein said analyte is prostate specific antigen (PSA).

4. The method of claim 1, wherein said analyte is comprised in a sample of a subject.

5. The method of claim 1, wherein said capture agent is an agent specifically binding to said analyte.

6. The method of claim 1, wherein said capture agent is an antibody, or a derivative thereof.

7. The method of claim 1, wherein said cleaving at least one covalent bond comprises enzymatically hydrolyzing at least one covalent bond within said analyte.

8. The method of claim 1, wherein said cleaving at least one covalent bond within said analyte comprises contacting said analyte with at least one protease.

9. The method of claim 1, wherein said cleaving at least one covalent bond within said analyte comprises contacting said analyte with an endopeptidase.

10. The method of claim 1, wherein said cleaving at least one covalent bond within said analyte comprises contacting said analyte with Trypsin.

11. The method of claim 1, wherein said at least one further step of deglycosylation of said analyte comprises contacting said analyte with an endoglycosidase.

12. The method of claim 1, wherein said at least one further step of deglycosylation of said analyte comprises contacting said analyte with Endo F3.

13. The method of claim 1, wherein said detecting comprises detecting said analyte or fragments thereof by mass spectrometry (MS).

14. The method of claim 1, wherein said detecting comprises detecting said analyte or fragments thereof by liquid chromatography (LC)-coupled mass spectrometry (LC-MS).

15. A method for detecting PSA and treating prostate cancer in a human subject, the method comprising
   a) contacting a sample from the human subject comprising PSA, a capture agent and a solid surface to form a capture complex comprising said PSA and said capture agent attached to said solid surface,
   b) cleaving at least one covalent bond within said PSA and/or within said capture agent comprised in said capture complex and, thereby, releasing said PSA or a fragment thereof from said capture complex,
   c) detecting said PSA or fragment thereof and, thereby, detecting said PSA, wherein said capture agent is attached to said solid surface simultaneously to contacting said capture agent with said PSA, wherein said method comprises a step of deglycosylation of said PSA bound to said capture agent, and
   d) comparing an amount of PSA detected from the sample from the human subject to a reference and diagnosing the presence of prostate cancer based upon the comparison, and
   e) treating said human subject diagnosed with prostate cancer.

* * * * *

SEQUENCE LISTING

<160> NUMBER OF SEQ ID NOS: 1

<210> SEQ ID NO 1
<211> LENGTH: 12
<212> TYPE: PRT
<213> ORGANISM: Homo sapiens

<400> SEQUENCE: 1

Leu Ser Glu Pro Ala Glu Leu Thr Asp Ala Val Lys
1               5                   10